US 7,640,784 B2

(12) United States Patent
Feng (10) Patent No.: US 7,640,784 B2
(45) Date of Patent: Jan. 5, 2010

(54) SYSTEM FOR CALIBRATING DISSOLVED OXYGEN ANALYZERS USING COMPRESSED FLUIDS DURING CLEANING

(75) Inventor: Chang-Dong Feng, Long Beach, CA (US)

(73) Assignee: Rosemount Analytical Inc., Irvine, CA (US)

( * ) Notice: Subject to any disclaimer, the term of this patent is extended or adjusted under 35 U.S.C. 154(b) by 244 days.

(21) Appl. No.: 11/522,828

(22) Filed: Sep. 18, 2006

(65) Prior Publication Data

US 2008/0067065 A1 Mar. 20, 2008

(51) Int. Cl.
*G12B 13/00* (2006.01)
(52) U.S. Cl. .......................... 73/1.06; 73/1.07
(58) Field of Classification Search ................. 73/1.06, 73/1.07
See application file for complete search history.

(56) References Cited

U.S. PATENT DOCUMENTS 7,300,630 B2 * 11/2007 Cronin et al. ................. 422/82

OTHER PUBLICATIONS

"Dissolved Oxygen Measurement System with Air Blast Cleaner", Product Data Sheet PDS 71-DO-03/04/rev.D, Rosemount Analytical, Aug. 2004, 6 pages.*

Lu, R. et al., "Fabrication and Evaluation of an Oxygen Microelectrode Applicable to Environmental Engineering and Science", J. Environ. Eng. Sci. vol. 1, 2002, pp. 225-235.*
"Dissolved Oxygen Measurement in Wastewater Treatment—Two Different Technologies," Application Data Sheet ADS4950-01/rev E, Rosemount Analytical, Jan. 2006, 3 pages.
"Conductivity, pH/ORP, & Amperometric HART Analyzers/Controllers: Model 54e Family of Analyzers/Controllers," Product Data Sheet 71-54e/rev. H, Rosemount Analytical, Jan. 2006, 11 pages.
"Dissolved Oxygen Measurement in Municipal Wastewater," Rosemount Analytical, 2005.
"Improve Performance and Reduce Maintenance Costs: Model Q45D Dissolved Oxygen Monitor," Analytical Technology, Inc., May 2005, 6 pages.

* cited by examiner

*Primary Examiner*—Daniel S Larkin
(74) *Attorney, Agent, or Firm*—Christopher R. Christenson; Westman, Champlin & Kelly, P.A.

(57) ABSTRACT

A dissolved oxygen measurement system, and a method for calibrating a dissolved oxygen analyzer are provided. The method includes directing a pressurized cleaning fluid, having a known oxygen content, upon a sensing surface of a dissolved oxygen sensor disposed in a fluid. Then, the analyzer waits until the dissolved oxygen sensor response to the pressurized cleaning fluid is relatively stable, and stores a calibration value relative to the dissolved oxygen sensor response to the pressurized cleaning fluid. A dissolved oxygen measurement system is also provided. The system includes a dissolved oxygen sensor disposed in a fluid and a first source of a first compressed cleaning fluid that has a first dissolved oxygen content. A dissolved oxygen analyzer is coupled to the dissolved oxygen sensor and to the first valve and is configured to obtain a first calibration value related to the first dissolved oxygen content.

9 Claims, 7 Drawing Sheets

SYSTEM FOR CALIBRATING DISSOLVED OXYGEN ANALYZERS USING COMPRESSED FLUIDS DURING CLEANING

BACKGROUND OF THE INVENTION

Waste water treatment plants generally separate solids from the liquid and generally consist of two basic stages: primary treatment and secondary treatment. In the primary treatment stage, larger solids are removed from waste water by settling. Secondary treatment is a large biological process for further removal of the remaining suspended and dissolved solids. Secondary treatment removes up to 85% of the remaining organic material through a biological process and cultivating and adding sewage microorganisms to the waste water. This process is accomplished in a trickling filter or an aeration tank.

Waste water treatment plants generally use aeration tanks to suspend microorganisms in waste water. After leaving the primary treatment stage, sewage is pumped into aeration tanks. The sludge is loaded with microorganisms and mixed with air or pure oxygen. As air is forced into the aeration basins, the air increases the activity of these microorganisms and helps keep the organic waste thoroughly mixed.

Dissolved oxygen (DO) is added to the aeration basin to enhance the oxidation process by providing oxygen to aerobic microorganisms so that they can successfully turn organic wastes into inorganic byproducts. In order to effectively metabolize food and reproduce, each microorganism generally requires at least 0.1 to 0.3 mg/L DO. Most waste water treatment plants maintain about 2 mg/L of DO so that the microorganisms contained in the floc can get sufficient oxygen. A floc is generally a clump of solids formed in sewage by biological or chemical action. If the dissolved oxygen is less than 2 mg/L, the microorganisms in the center of the floc may die since the microorganisms on the outside of the floc use the DO first. If this happens, the floc breaks up. If the DO content is too low, the environment is not stable for these microorganisms and they will die due to anaerobic zones, the sludge will not be properly treated, and the waste water treatment plant will be forced to conduct an expensive and time-consuming biomass replacement process. Because of this risk, many waste water treatment plants compensate by adding excessive amounts of dissolved oxygen to their process. However, when the dissolved oxygen levels become too high, energy is wasted, expensive aeration equipment undergoes unnecessary usage, and unwanted microorganisms (filamentous biology) are prompted.

Power costs associated with the operation of the aeration process and secondary treatment generally run from 30 to 60% of the total electrical power used by a typical waste water treatment facility. Equipping the aeration basin with on-line dissolved oxygen measurement automates the aeration system to maintain the correct amount of dissolved oxygen. Further, waste water treatment plant energy costs may be reduced significantly by using on-line dissolved oxygen measurement.

Dissolved oxygen introduced into the aeration basins also provides the added benefit of mixing, thus bringing the microorganisms, oxygen and nutrients together. Mixing also removes metabolic waste products. Finally, the mixing or aeration keeps this floc suspended and prevents it from settling to the bottom.

Continuous and precise measurement of dissolved oxygen is cost effective, keeps the waste treatment process functioning properly, and eliminates the need for frequent sampling and laboratory sampling.

Various types of dissolved oxygen sensors are known. However, all dissolved oxygen sensors stop working effectively when they become coated with biofilm or a slime layer. Thus, such sensors generally require regular cleaning (weekly or more often) in order to ensure that the dissolved oxygen can be efficiently sensed. In order to easily clean dissolved oxygen sensors, it is known to use pressurized gas and a nozzle pointing at the sensing surface of the dissolved oxygen sensor to remove the biofilm or sludge from the sensing surface. For example, the model DO-03/04 Dissolved Oxygen Measuring System with Air Blast Cleaner, available from Rosemount Analytical, Inc., of Irvine, Calif., provides a complete system including a sensor, analyzer, sensor washer head, mount hardware, and air compressor. This complete system automatically generates air blasts that remove any biofilm, slime or sludge that may have accumulated upon the sensor. However, while this automated system is highly convenient, the sensor may still require periodic calibration in order to ensure that its readings are accurate.

During calibration, a fluid (gas or liquid) with a known dissolved oxygen content is exposed to the dissolved oxygen sensor. Then, the response of the dissolved oxygen sensor to the known quantity is recorded and used to compensate, or otherwise adjust, later-read values of the dissolved oxygen sensor during operation. Field maintenance in waste water treatment facilities is relatively unpleasant, and generally the less one has to be exposed to such substances, the better. Providing a dissolved oxygen measurement system with the ability to reduce technician effort and expense required for periodic calibration would represent a significant benefit to the art.

SUMMARY OF THE INVENTION

A dissolved oxygen measurement system, and a method for calibrating a dissolved oxygen analyzer are provided. The method includes directing a pressurized cleaning fluid, having a known oxygen content, upon a sensing surface of a dissolved oxygen sensor disposed in a fluid. Then, the analyzer waits until the dissolved oxygen sensor's response to the pressurized cleaning fluid is relatively stable, and stores a calibration value relative to the dissolved oxygen sensor's response to the pressurized cleaning fluid. A dissolved oxygen measurement system is also provided. The system includes a dissolved oxygen sensor disposed in a fluid and a first source of a first compressed cleaning fluid that has a first dissolved oxygen content. A first valve is operably coupled to the first source and configured to selectively direct the first compressed cleaning fluid against a sensing surface of the dissolved oxygen sensor. A dissolved oxygen analyzer is coupled to the dissolved oxygen sensor and to the first valve and is configured to obtain a first calibration value related to the first dissolved oxygen content while the first valve directs the first cleaning fluid against the sensing surface.

DETAILED DESCRIPTION OF ILLUSTRATIVE EMBODIMENTS

Figure 1:
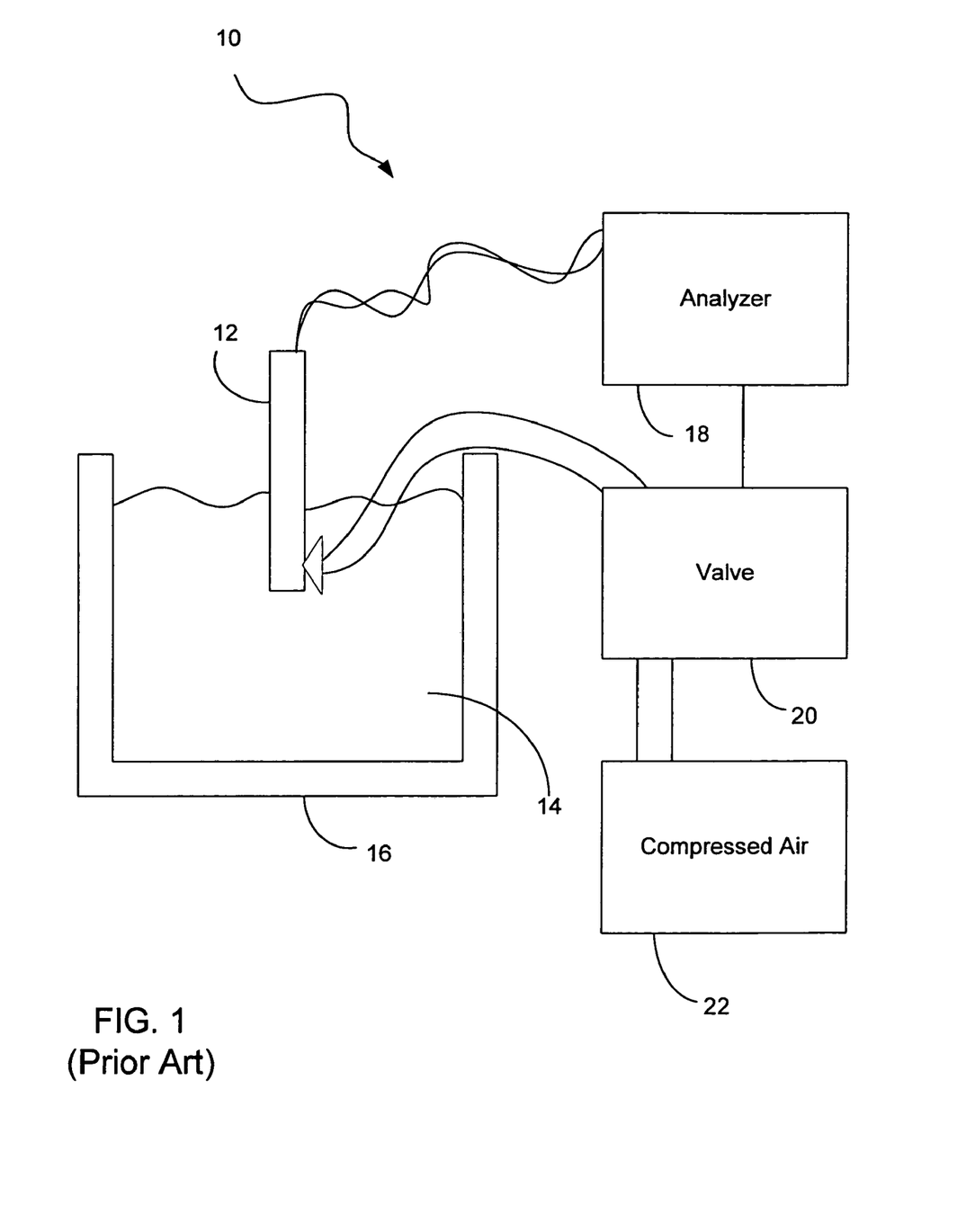
FIG. 1 is a diagrammatic view of a dissolved oxygen measurement system with an air blast cleaner with which embodiments of the present invention are particularly useful.

FIG. 1 is a diagrammatic view of a dissolved oxygen sensing system suitable for waste water treatment applications. System 10 includes dissolved oxygen sensor 12 disposed within waste water 14 in aeration basin 16. DO sensor 12 may be any suitable sensor, but is preferably a Model 499 ADO dissolved oxygen sensor, available from Rosemount Analytical, Inc. Sensor 12 is coupled to a suitable dissolved oxygen analyzer 18. Analyzer 18 may be any suitable dissolved oxygen analyzer, but is preferably a Model 54 eA dissolved oxygen analyzer available from Rosemount Analytical, Inc. Analyzer 18 is coupled to valve 20 such that valve 20 operates based upon an energization signal provided, or inhibited, by analyzer 18. Valve 20 is coupled to source 22 of compressed air 22. Source 22 may be an air compressor, or any other suitable device that is able to provide a gas at an elevated pressure. Source 22 is coupled to valve 20 such that compressed air can be selectively provided to sensor 12 based upon energization of valve 20 by analyzer 18. The compressed air provided by valve 20 is configured, in any suitable manner, to be directed at one or more sensing surfaces of sensor 12.

The elements of system 10, illustrated in FIG. 1, may comprise the Model DO-03/04 Dissolved Oxygen Measurement System with Air Blast Cleaner, available from Rosemount Analytical, Inc. However, variations can exist in the sensor, the analyzer, the valve, and the source of compressed air as embodiments of the present invention, which will be described in greater detail below, are practiced.

Figure 2:
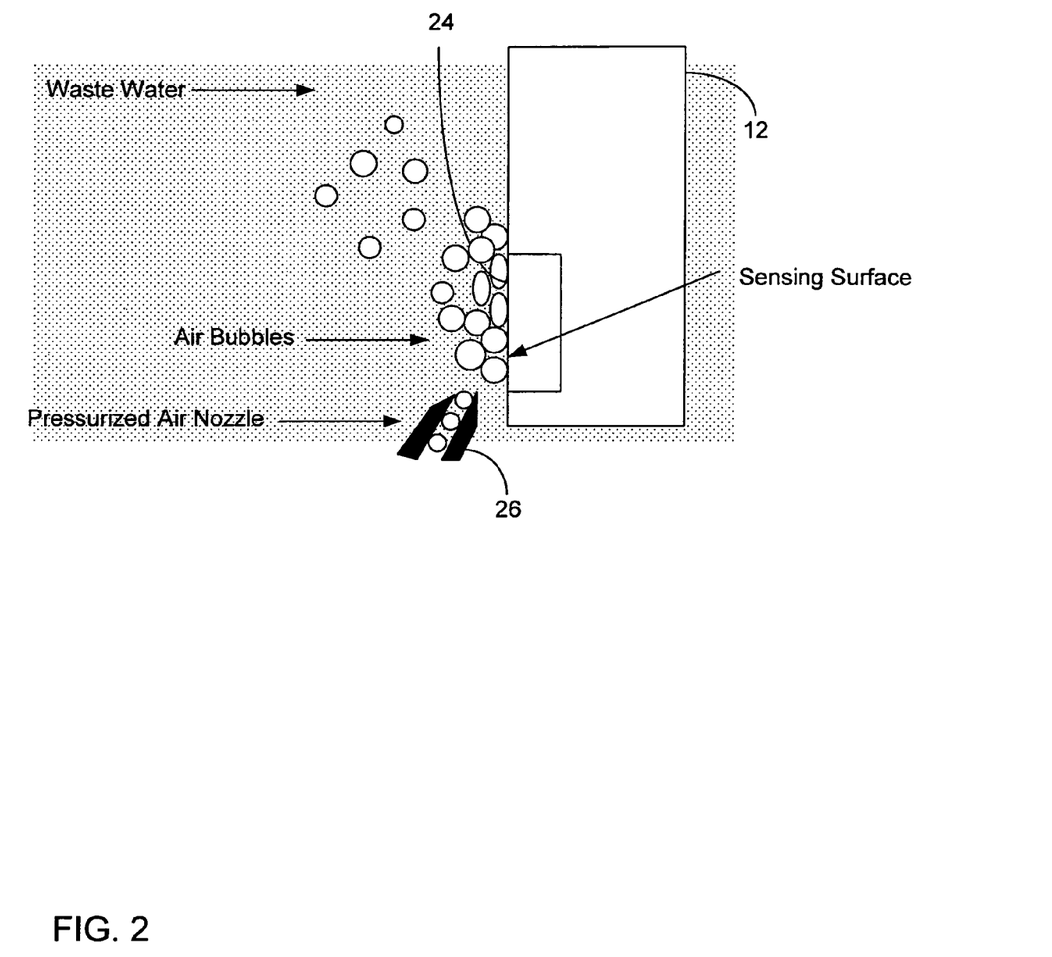
FIG. 2 is a diagrammatic view of an air blast cleaning a sensing surface of a dissolved oxygen sensor.

FIG. 2 is a diagrammatic view of a portion of dissolved oxygen sensor 12 disposed within waste water 14. Sensor 12 includes a sensing surface 24 which is used to actually sense the dissolved oxygen in accordance with known techniques. A nozzle 26 is disposed to direct pressurized air, or some other suitable fluid, upon sensing surface 24 periodically, or as desired, in order to remove biofilm or sludge buildup on sensing surface 24.

In accordance with an embodiment of the present invention, as the pressurized air is brought into contact with the sensing surface 24, analyzer 18 can actually be recalibrated based upon contact between the pressurized air and sensing surface 24. Thus, periodic manual recalibration of the dissolved oxygen sensor via manual methods are no longer required. Instead, analyzer 18 can actually be recalibrated each and every time that nozzle 26 directs pressurized air upon sensing surface 24. Certainly, calibration can be effected in larger intervals than the air-blast intervals.

Figure 3:
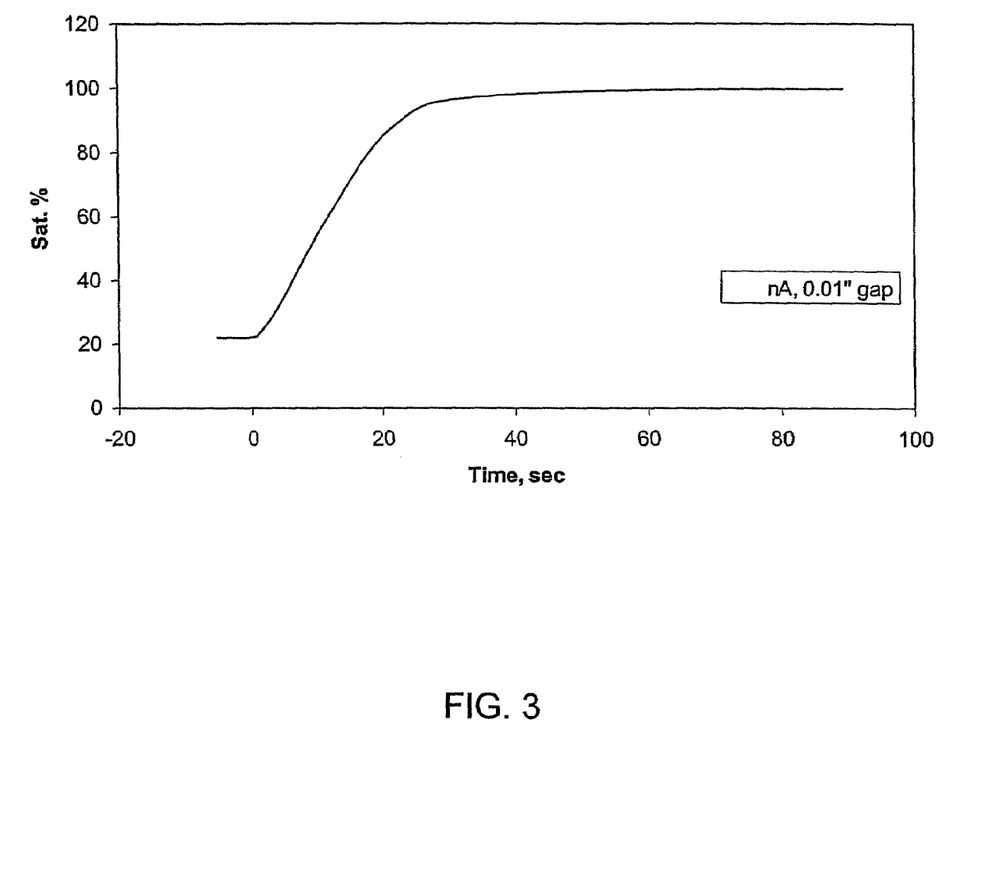
FIG. 3 is a chart of dissolved oxygen sensor response during an air blast.

FIG. 3 is a chart of sensor response versus time when pressurized air is blasted against sensing surface 24. As can be seen, at zero seconds the sensor response is approximately 20% saturation. As the pressurized air continues to contact sensing surface 24, the sensor response rises based upon sensor 12 sensing the oxygen in the pressurized air. At approximately twenty seconds, most of the sensor response has changed with the sensor response reading approximately 85% saturation. Subsequently, after forty seconds have elapsed, the sensor response has substantially flattened at approximately 100% saturation. Accordingly, at this time, the dissolved oxygen analyzer can be recalibrated for its maximum saturation. Conversely, if the pressurized gas is controlled to include no oxygen whatsoever, the analyzer could recalibrate its zero point. While much of the description of the pressurized fluid has been with respect to pressurized air, any suitable fluid (liquid or gas) can be used as long as the dissolved oxygen characteristic of the pressurized fluid is known. Thus, even a liquid with a known dissolved oxygen content could be used to effect the pressurized blast and applied long enough until the dissolved oxygen sensor settled, and the analyzer could be calibrated for the known dissolved oxygen content. Certainly, pressurized air is preferred in that it does not introduce any undesirable or unknown materials into the waste water.

Figure 4:
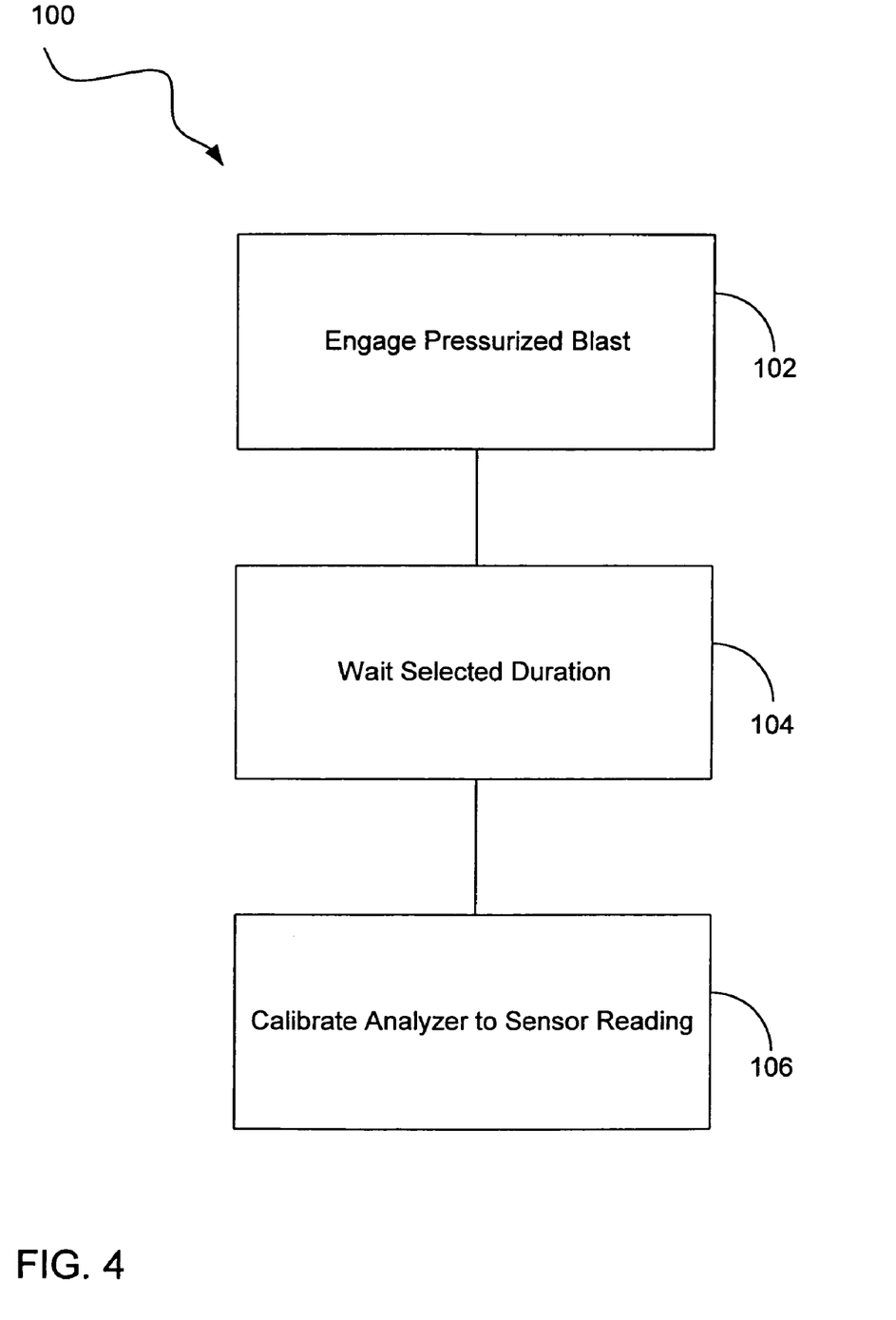
FIG. 4 is a flow diagram of a method of calibrating a dissolved oxygen measurement system in accordance with an embodiment of the present invention.

FIG. 4 is a flow diagram of a method of calibrating a dissolved oxygen analyzer in accordance with an embodiment of the present invention. Method 100 begins at block 102 where the analyzer, such as analyzer 18, generates or otherwise causes or observes a pressurized blast. This blast is preferably in the form of an energization signal sent to valve 20 to allow compressed air from compressed air source 22 to be directed through a pressurized nozzle, such as nozzle 26, upon a sensing surface 24 of the dissolved oxygen sensor. Once the pressurized blast is engaged, method 100 continues at block 104 where the analyzer waits a selected duration. For example, referring to FIG. 3, the selected duration may be forty seconds. This provides sufficient time for the sensor response to stabilize, or otherwise flatten its response to the pressurized fluid. Once the selected duration has elapsed, method 100 continues at block 106 where analyzer 18 recalibrates itself based upon the sensor reading. Thus, if the compressed air is known to contain oxygen, analyzer 18 can periodically recalibrate its full saturation point. Method 100 can be executed each time an air blast is effected to clean the sensing surface; can be effected on suitable multiples of the air-blast cycles; or can be effected at any suitable duration.

Figure 5:
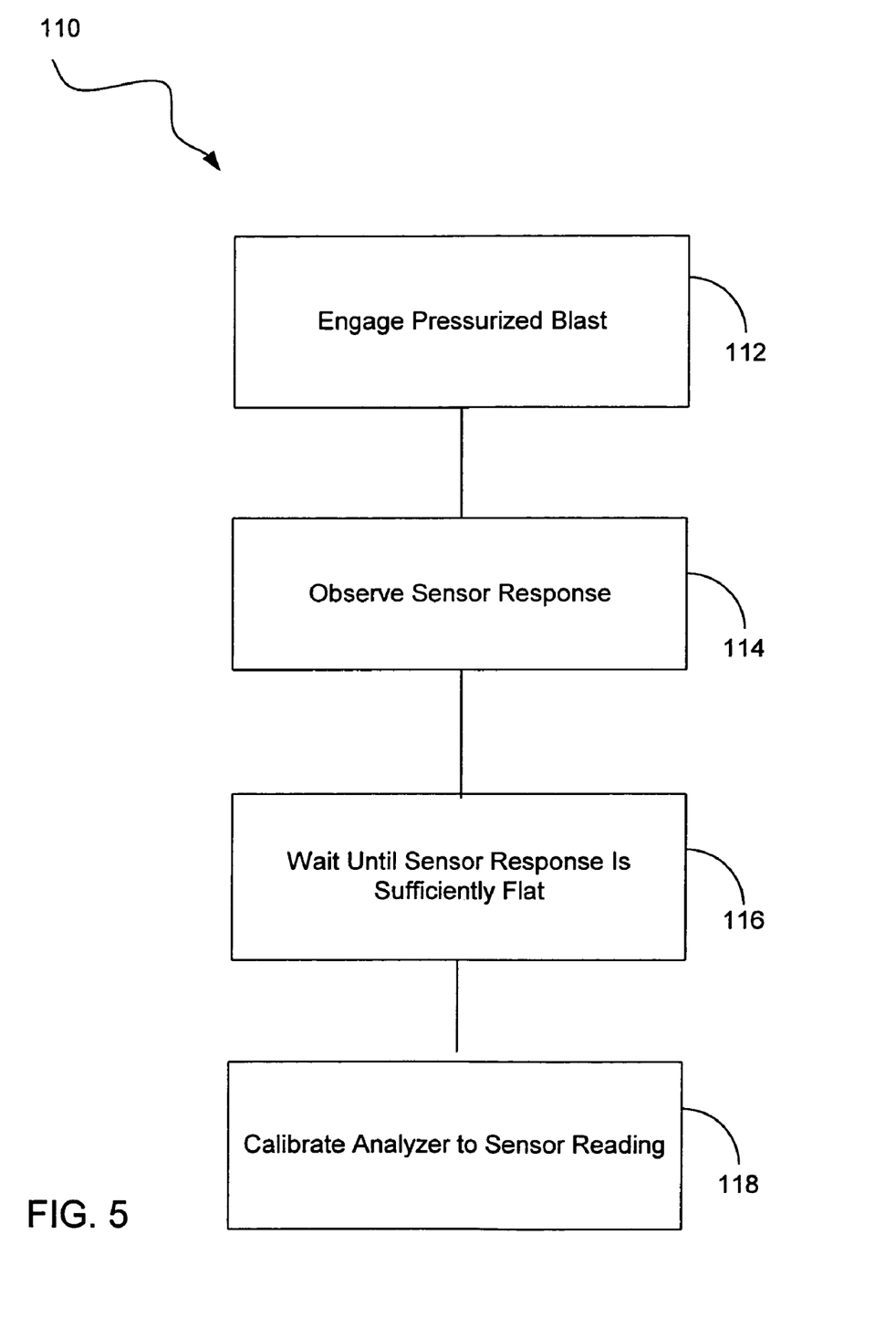
FIG. 5 is a flow diagram of a method of calibrating a dissolved oxygen measurement system in accordance with another embodiment of the present invention.

FIG. 5 is a flow diagram of a method 110 of calibrating a dissolved oxygen analyzer in accordance with another embodiment of the present invention. Method 110 begins at block 112, which may be the same as block 102, described above. While the pressurized blast is directed at the sensing surface of the dissolved oxygen sensor, analyzer 18 observes the sensor response, at block 114. Method 110 continues at block 116 where analyzer 18 waits until the sensor response is sufficiently flat, or otherwise has stabilized. In this manner, the actual timing may vary, depending on whether the sensor stabilizes very quickly, or takes much longer to stabilize. This approach may be more responsive to dynamically changing conditions relative to the oxygen content of the air, the actual pressure of the compressed air, the density and/or viscosity of the waste water, or other variables. Any suitable test can be used to determine whether the sensor response is sufficiently flat. For example, analyzer 18 can determine the rate of change of the sensor response and wait until the rate of change is sufficiently small. Once the sensor response is sufficiently flat at block 116, control passes to block 118 where analyzer 18 calibrates itself to the sensor reading.

Figure 6:
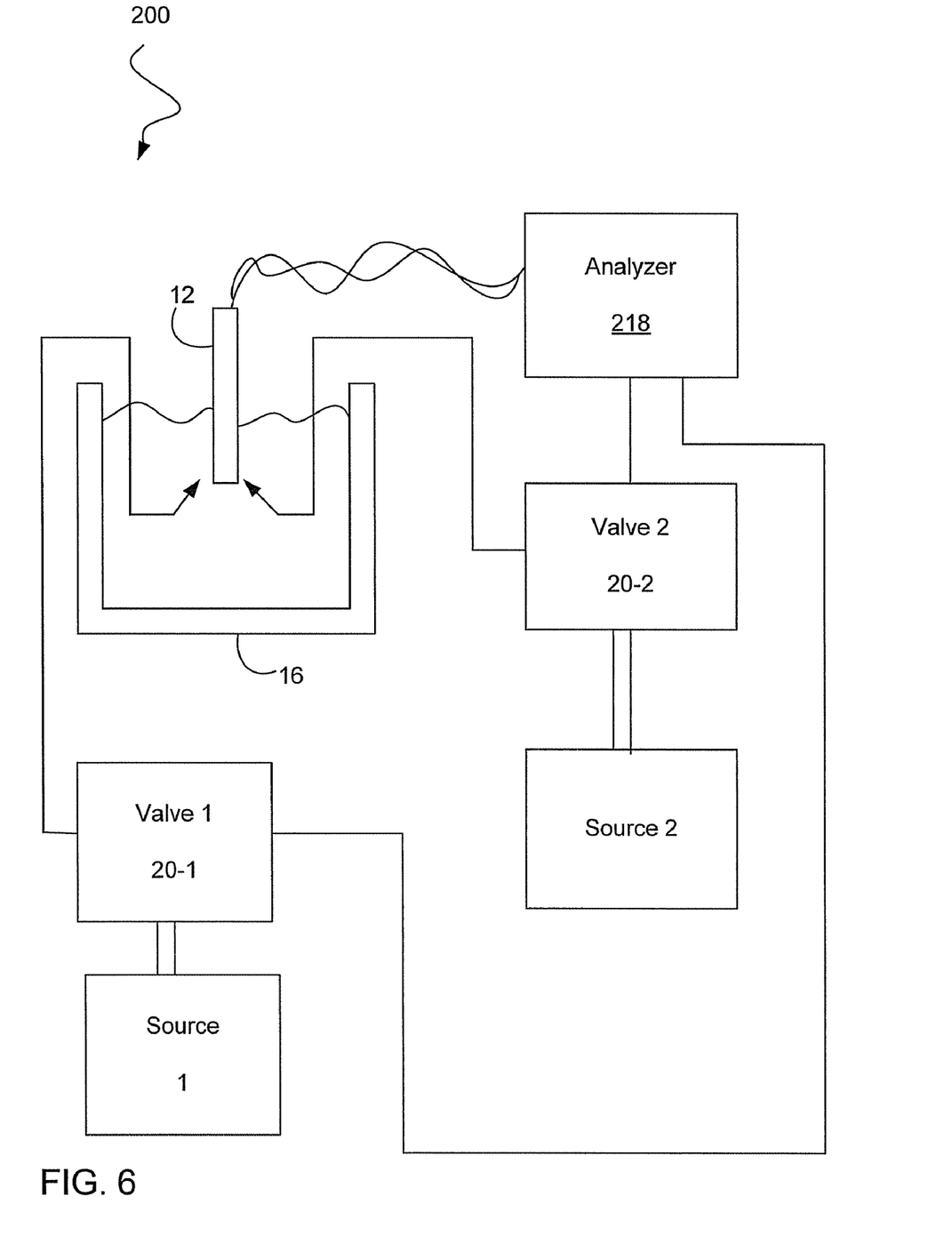
FIG. 6 is a diagrammatic view of a dissolved oxygen measurement system in accordance with an embodiment of the present invention.

FIG. 6 is a diagrammatic view of a dissolved oxygen measurement system in accordance with an embodiment of the present invention. System 200 includes many similar components to system 10, and like components are numbered similarly. Analyzer 218 differs from analyzer 18 in that analyzer 218 is configured to couple to a plurality of valves, 20-1 and 20-2. Each valve is coupled to a different respective source of pressurized fluid. Thus, analyzer 218 is able to direct different pressurized fluids upon sensor 12 depending on which valve, 20-1 or 20-2 is engaged. This allows analyzer 218 to recalibrate both its maximum span value as well as its zero value (assuming that the pressurized fluid in one source provides significant dissolved oxygen, and the other source provides no dissolved oxygen).

Figure 7:
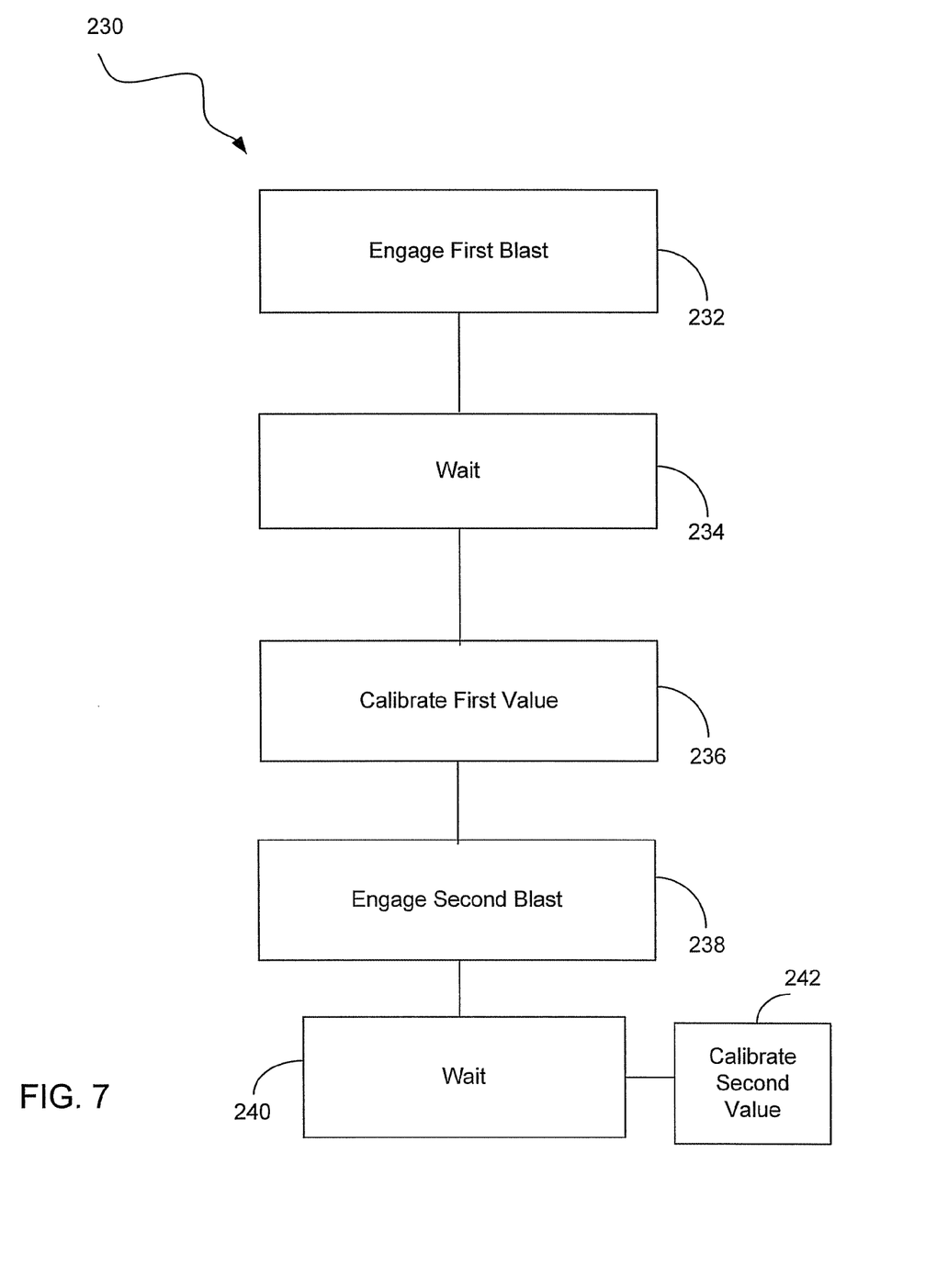
FIG. 7 is a flow diagram of a method of calibrating a dissolved oxygen measurement system in accordance with an embodiment of the present invention.

FIG. 7 is a flow diagram of a method of calibrating a dissolved oxygen measurement system in accordance with an embodiment of the present invention. Method 230 begins at block 232 where analyzer 218 generates a first pressurized fluid blast against the dissolved oxygen sensor. At block 234, analyzer 218 waits until the sensor response has stabilized. Block 234 can be performed using timing methods set forth above, sensor signal processing methods, or any combination thereof. Once the sensor has stabilized its response to the ongoing pressurized fluid blast, analyzer 218 calibrates a first value related to the dissolved oxygen content from the first blast, as indicated at block 236. Then, analyzer 218 stop the first blast and generates a second blast of pressurized fluid from a different source, as indicated at block 238. Next, analyzer 218 waits until the dissolved oxygen sensor response has sufficiently stabilized during the second blast, as indicated at block 240. Once this occurs, analyzer 218 calibrates itself to a second value based upon a known dissolved oxygen content (which can be any value between 0 and 100% dissolved oxygen), as indicated at block 242.

The calibration values are stored in the analyzer and used during subsequent operation to compensate, or otherwise adjust, the readings of dissolved oxygen sensor. Thus, the periodic blasts not only clean the dissolved oxygen sensor, but also allow recalibration of the analyzer at relatively frequent intervals. This reduces the efforts and time required by maintenance technicians, while also potentially increasing sensor accuracy.

Although the present invention has been described with reference to preferred embodiments, workers skilled in the art will recognize that changes may be made in form and detail without departing from the spirit and scope of the invention.

What is claimed is:

1. A method for calibrating a dissolved oxygen analyzer, the method comprising:
    directing a pressurized cleaning fluid, having a known oxygen content, upon a sensing surface of a dissolved oxygen sensor disposed in a liquid;
    waiting a selected duration after commencement of directing the pressurized cleaning fluid upon the sensing surface; and
    storing a calibration value in the analyzer relative to the dissolved oxygen sensor response to the pressurized fluid.

2. The method of claim 1, wherein the pressurized cleaning fluid is compressed air.

3. The method of claim 1, wherein directing the pressurized cleaning fluid is generated by the analyzer energizing a valve coupled to a source of pressurized cleaning fluid.

4. The method of claim 1, wherein directing the pressurized cleaning fluid is generated by energizing a source of cleaning pressurized fluid.

5. The method of claim 4, wherein the source of pressurized cleaning fluid is an air compressor.

6. The method of claim 1, wherein the calibration value is a maximum saturation value.

7. The method of claim 1, wherein the calibration value is a zero value.

8. The method of claim 1, wherein the method is performed each time pressurized cleaning fluid is directed at the dissolved oxygen sensor.

9. The method of claim 1, wherein the method is performed less frequently than each time pressurized cleaning fluid is directed at the dissolved oxygen sensor.

* * * * *

UNITED STATES PATENT AND TRADEMARK OFFICE
CERTIFICATE OF CORRECTION

PATENT NO.        : 7,640,784 B2
APPLICATION NO. : 11/522828
DATED             : January 5, 2010
INVENTOR(S)       : Chang-Dong Feng Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 353 days.

Signed and Sealed this

Sixteenth Day of November, 2010

David J. Kappos
*Director of the United States Patent and Trademark Office*